United States Patent [19]

Kitao et al.

[11] Patent Number: 4,833,256

[45] Date of Patent: May 23, 1989

[54] FLUORAN DERIVATIVES AND RECORDING MATERIAL CONTAINING THE SAME

[75] Inventors: Teijiro Kitao, Tondabayashi; Tetsuhiko Yamaguchi, Hadano; Katsumi Murofushi, Yokohama; Masato Futagami, Kawasaki; Nobuyuki Nagato, Wako; Kunio Imamura, Tokorozawa, all of Japan

[73] Assignee: Showa Denko Kabushiki Kaisha, Tokyo, Japan

[21] Appl. No.: 916,686

[22] Filed: Oct. 8, 1986

[30] Foreign Application Priority Data

Oct. 8, 1985 [JP] Japan ................ 60-222726
Nov. 21, 1985 [JP] Japan ................ 60-259815

[51] Int. Cl.$^4$ ................ C07D 311/88; C07D 311/96
[52] U.S. Cl. ................ 549/227; 549/225; 549/226
[58] Field of Search ................ 549/227, 226, 225

[56] References Cited

U.S. PATENT DOCUMENTS

| | | | |
|---|---|---|---|
| 3,925,416 | 12/1975 | Akamatsu et al. | 549/226 |
| 4,012,419 | 3/1977 | Vincent et al. | 549/225 |
| 4,410,708 | 10/1983 | Yahagi et al. | 549/225 |
| 4,603,202 | 7/1986 | Moyer et al. | 549/226 |
| 4,612,558 | 9/1986 | Anzai et al. | 549/226 |
| 4,694,088 | 9/1987 | Kaneko et al. | 549/226 |

FOREIGN PATENT DOCUMENTS 012654 7/1984 Japan ................ 549/226

*Primary Examiner*—Richard L. Raymond
*Assistant Examiner*—Patricia L. Morris
*Attorney, Agent, or Firm*—Sughrue, Mion, Zinn, Macpeak & Seas

[57] ABSTRACT

A fluoran derivative useful for a heat-sensitive recording material, having the following general formula I;

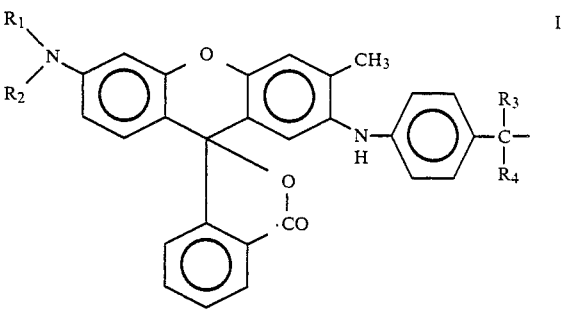

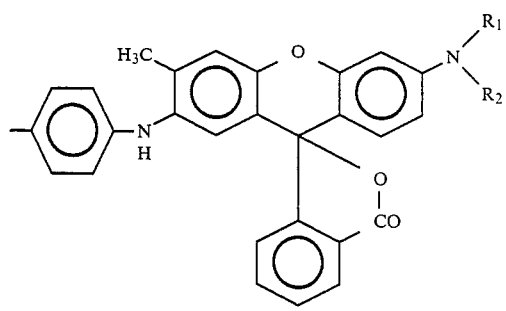

wherein $R_1$ and $R_2$, which may be the same or different, stand for an alkyl group having 1 to 9 carbon atoms, a cycloalkyl group having 3 to 6 carbon atoms, a phenyl group or a phenyl group substituted by an alkyl group having 1 to 4 carbon atoms, and $R_3$ and $R_4$, which may be the same or different, stand for an alkyl group having 1 to 6 carbon atoms or a phenyl group or $R_3$ and $R_4$ may form a 5- to 8-membered cycloalkane together with the carbon atom to which they are bonded.

3 Claims, No Drawings

FLUORAN DERIVATIVES AND RECORDING MATERIAL CONTAINING THE SAME

BACKGROUND OF THE INVENTION

1. Field of the Invention

The present invention relates to novel fluoran derivatives, a process for the preparation thereof and a recording material containing the derivatives as a heat-sensitive coloring component.

2. Description of the Related Art

Heat-sensitive recording materials comprising an electron-donative fluoran dye and an electron-receptive compound are well-known (see, for example, Japanese Examined Patent Publication No. 51-23204, Japanese Unexamined Patent Publication No. 57-31591, Japanese Unexamined Patent Publication No. 58-52356 and Japanese Unexamined Patent Publication No. 60-36568). As the fluoran dye, there can be mentioned 3-N,N-diethylamino-7-o-chloroanilinofluoran and 3-(N-methyl-N-cyclo-hexylamino)-6-methyl-7-anilinofluoran as the color former.

The properties that should be at least possessed by such recording materials are as follows.

(1) The coloration density and coloration sensitivity are sufficient.

(2) Fogging is not caused.

(3) The colored body after the color development has a sufficient fastness.

However, recording materials capable of satisfying all of these requirements sufficiently have not been developed.

A heat-sensitive recording paper comprising a known fluoran dye as mentioned above is defective in that when a plasticizer, an oil or an organic solvent falls in contact with a colored portion, the color comes off.

SUMMARY OF THE INVENTION

We made research with a view to overcoming the defect of conventional fluoran type dyes, and as the result, we found that if a novel compound obtained by condensation of a specific fluoran compound with a ketone is used as the heat-sensitive coloring component, the fastness of the colored portion of the obtained recording material is highly improved. We have now completed the present invention based on this finding.

In accordance with the present invention, there are provided fluoran derivatives of the following general formula:

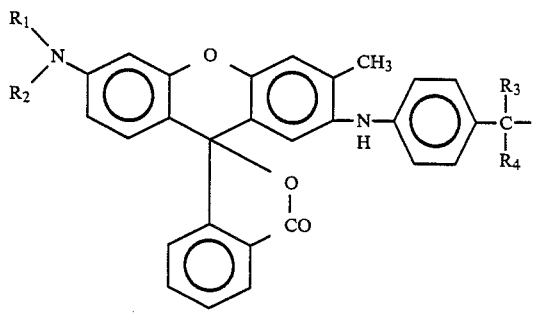

I

-continued

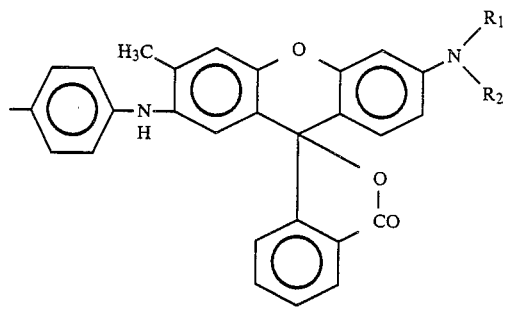

wherein $R_1$ and $R_2$, which may be the same or different, stand for an alkyl group having 1 to 9 carbon atoms, a cycloalkyl group having 3 to 6 carbon atoms, a phenyl group or a phenyl group substituted by an alkyl group having 1 to 4 carbon atoms, and $R_3$ and $R_4$, which may be the same or different, stand for an alkyl group having 1 to 6 carbon atoms or a phenyl group or $R_3$ and $R_4$ may form a 5- to 8-membered cycloalkane together with the carbon atom to which they are bonded.

DESCRIPTION OF THE PREFERRED EMBODIMENTS

The fluoran derivatives of the present invention are relatively low in the solubility n plasticizers, oils and organic solvents. Accordingly, the fastness of the colored portion of the heat-sensitive recording material is highly improved. Furthermore, the fluoran derivatives per se are a substantially white substance, but they have such a property that if they are intimately contacted with an electron-receptive substance (color developer) such as bisphenol A or silica gel, they form a good black color. Therefore, the fluoran derivatives of the present invention are very valuable as a heat-sensitive coloring component.

In the compounds represented by the general formula I, the alkyl group as $R_1$ and $R_2$ or $R_3$ and $R_4$ may be linear or branched. When $R_3$ and $R_4$ form a cycloalkane together with the carbon atom to which they are bonded, as examples of the cycloalkane, there can be mentioned cyclopentanone, cyclohexanone, cycloheptanone and cyclooctanone.

As preferred examples of the group

in the compound represented by the general formula I, the following groups can be mentioned:

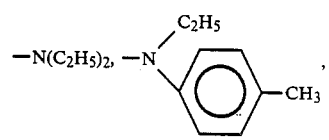

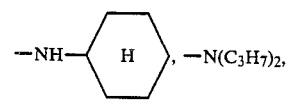

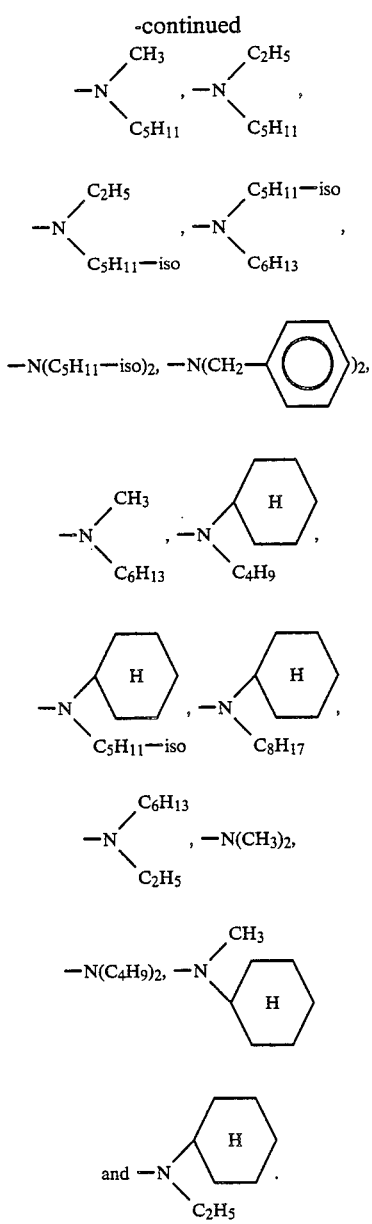

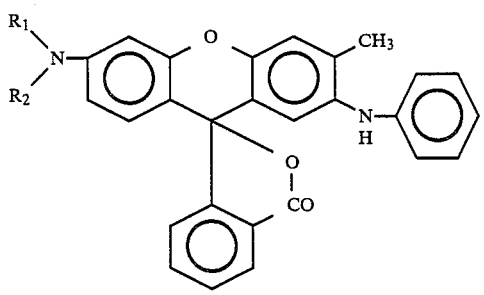

The fluoran derivatives represented by the general formula I can be prepared by reacting 2 moles of a compound of the following general formula II:

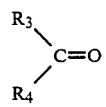

wherein $R_3$ and $R_4$ are as defined above.

More specifically, 2 moles of a fluoran compound represented by the general formula II is reacted with 1 mole of a ketone at 30° to 80° C. for 5 to 100 hours, optionally in the presence of a catalyst such as ferric chloride, calcium chloride, boric acid, hydrogen sulfide or an alkylmercaptan, by using a condensing agent such as sulfuric acid, hydrochloric acid or phosphoric acid. The reaction mixture is poured into ice water, and after neutralization, the precipitate is recovered by filtration and dissolved in ethyl acetate. The solution is washed with a 2% aqueous solution of sodium hydroxide, concentrated and recrystallized from an organic solvent such as toluene, benzene, isopropyl alcohol or acetone to obtain an intended compound at a high purity. In the reaction, if a polar solvent such as acetonitrile, tetrahydrofuran or dioxane is used as the reaction medium, the desired product may be obtained with a higher yield.

A recording material can be prepared by using the fluoran derivatives represented by the general formula I as a heat-sensitive coloring component according to a known process. For example, a heat-sensitive recording material can be obtained by using the compounds of the general formula I according to a process taught in the specification of U.S. Pat. Nos. 2,548,366, 2,800,457 or 2,800,458.

When the fluoran derivative of the present invention is used as a heat-sensitive coloring component, there can be obtained a heat-sensitive recording material in which the colored portion has an excellent fastness to a plasticizer, an oil, an organic solvent or the like.

A mixture of one or more of the fluoran derivatives of the present invention with one or more of the known fluoran compounds as listed below may also be used as the heat-sensitive coloring component, thereby improving the shelf life and the coloring sensitivity of the resulting recording material. The examples of the fluoran compounds include 3-diethylamino-6-methyl-7-anilinofluoran, 3-dibutylamino-6-methyl-7-anilinofluoran, 3-(N-methyl-cyclohexylamino)-6-methyl-7-anilinofluoran, 3-(N-ethyl-p-tolyl)-6-methyl-7-anilinofluoran, 3-(N-ethyl-isoamyl)-6-methyl-7-anilinofluoran, 3-diethylamino-7-o-chloroanilinofluoran, and 3-dibutylamino-7-o-chloroanilinofluoran.

The present invention will now be described in detail with reference to the following examples.

Synthesis Example 1

In 4 ml of acetone, 4 ml of acetonitrile and 6 ml of concentrated hydrochloric acid was dissolved 1 g of 3-(N-methyl-N-cyclohexylamino)-6-methyl-7-anilinofluoran, and 0.1 g of ferric chloride was added to the solution and reaction was carried out at 60° to 65° C. for 5 hours. After completion of the reaction, the reaction liquid was poured into 30 ml of ice water, and after the neutralization, the precipitate was recovered by filtration. The filtrate was dissolved in chloroform and the solution was washed with a 2% aqueous solution of sodium hyroxide. The chloroform layer was separated, dehydrated with anhydrous sodium sulfate and concentrated. Subsequently, toluene was added to the concentrate and recrystallization was carried out to obtain 0.8 g of a condensation product in the form of a white power having a melting point of 237° to 239° C. From the result of the measurement of the molecular weight by gel permeation chromotography, it was found that the product was a condensation product of 2 moles of the starting fluoran compound, corresponding to the general formula I.

The product showed a black color on silica gel, and when it was contacted with bisphenol A, a blackish green color was developed.

Synthesis Example 2

In 2 ml of methylethylketone, 4 ml of acetonitrile and 7 ml of concentrated hydrochloric acid was dissolved 1 g of 3-(N-methyl-N-cyclohexylamino)-6-methyl-7-anilinofluoran, and 0.1 g of ferric chloride was added to the solution and reaction was carried out at 70° to 75° C. for 10 hours. After completion of the reaction, post treatments were carried out in the same manner as described in Synthesis Example 1 to obtain 0.86 g of a condensation product in the form of a white powder having a melting point of 215° to 219° C. From the result of the measurement of the molecular weight of the product by gel permeation chromotography, it was found that the product was a condensation product of 2 moles of the starting fluoran compound, corresponding to the general formula I.

The product showed a black color, and when it was contacted with bisphenol A, a blackish green color was developed.

Synthesis Example 3

In 40 ml of acetone (purity 99.5%), 30 ml of dioxane and 60 ml of concentrated hydrochloric acid was dissolved 10 g of 3-(N-p-tolyl-N-ethylamino)-6-methyl-7-anilinofluoran (purity 99% or higher), and reaction was carried out at 60° to 65° C. for 5 hours. The liquid chromatography of the reaction mixture revealed that the conversion was 92% and the selectivity was 97%. After completion of the reaction, 150 ml of water was pored into the reaction mixture and after neutralization with an aqueous sodium hydroxide solution while cooling, the precipitate was filtered off. The precipitate was dispersed in a mixture of 80 ml of water and 120 ml of acetone, and the dispersion was agitated to wash the precipitate. The dispersion was filtered, the precipitate was dried, 70 ml of toluene was added, the precipitate was again washed while heating and filtered. Thus, 7.2 g of a condensation product was obtained, in the form of a white powder having a melting point of 263° to 269° C. From the result of the measurement of the molecular weight of the product by gel permeation chromotography, it was found that the product was a condensation product of 2 moles of the starting fluoran compound, corresponding to the general formula I.

The product showed a black color, and when it was contacted with bisphenol A, a blackish green color was developed.

Synthesis Example 4

In 5 ml of methylethylketone, 5 ml of acetonitrile and 5 ml of concentrated hydrochloirc acid was dissolved 1 g of 3-diethylamino-6-methyl-7-anilinofluoran, and 0.1 g of calcium chloride was added to the solution and reaction was carried out at room temperature for 3 days. After completion of the reaction, post treatments were carried out in the same manner as described in Synthesis Example 1 to obtain 0.5 g of a condensation product in the form of a white powder having a melting point of 199° to 204° C. From the result of the measurement of the molecular weight of the product by gel permeation chromatography, it was found that the product was a condensation product of 2 moles of the starting fluoran compound, corresponding to the general formula I.

The product showed a black color on silica gel and when it was contacted with bisphenol A, a blackish green color was developed.

Synthesis Example 5

In 5 ml of acetophenone, 5 ml of acetonitrile and 5 ml of concentrated hydrochloric acid was dissolved 1 g of 3-(N-methyl-N-cyclohexylamino)-6-methyl-7-anilinofluoran, and 0.1 g of calcium chloride was added to the solution and reaction was carried out at room temperature for 3 days. After completion of the reaction, post treatments were carried out in the same manner as described in Synthesis Example 1 to obtain 0.5 g of a condensation product in the form of a white powder having a melting point of 200° to 210° C. From the result of the measurement of the molecular weight of the product by gel permeation chromatography, it was found that the product was a condensation product of 2 moles of the starting fluoran compound, corresponding to the general formula I.

The product showed a black color and when it was contacted with bisphenol A, a blackish green color was developed.

Synthesis Examples 6 through 11

In the same manner as described in Synthesis Examples 1 through 5, fluoran derivatives shown in Table 1 were obtained by using appropriate staring materials.

In Table 1, the compounds as obtained in the above-mentioned Synthesis Examples 1 through 5 are also shown.

TABLE 1

| Synthesis Example No. | R₁ | R₂ | R₃ | R₄ | Developed Color Shade | Melting Point (°C.) |
|---|---|---|---|---|---|---|
| 1 | —CH₃ | cyclohexyl (H) | —CH₃ | —CH₃ | blackish green | 237–239 |
| 2 | —CH₃ | cyclohexyl (H) | —CH₃ | —C₂H₅ | blackish green | 215–219 |
| 3 | —C₂H₅ | —C₆H₄—CH₃ | —CH₃ | —CH₃ | blackish green | 263–269 |
| 4 | —C₂H₅ | —C₂H₅ | —CH₃ | —C₂H₅ | blackish green | 199–204 |
| 5 | —CH₃ | cyclohexyl (H) | —CH₃ | —C₆H₅ | blackish green | 200–210 |
| 6 | —CH₃ | cyclohexyl (H) | —CH₃ | —CH₂CH(CH₃)₂ | blackish green | 194–200 |
| 7 | —CH₃ | cyclohexyl (H) |  | —(CH₂)₅— | blackish green | 218–225 |
| 8 | —C₂H₅ | —C₂H₅ | —CH₃ | —CH₃ | blackish green | 199–205 |
| 9 | —C₂H₅ | —CH₂—CH₂—CH(CH₃)₂ | —CH₃ | —CH₃ | blackish green | 168–173 |
| 10 | " | " | —CH₃ | —C₂H₅ | blackish green | 168–175 |
| 11 | —C₂H₅ | —C₆H₄—CH₃ | —CH₃ | —C₂H₅ | blackish green | 239–245 |

The values of the hydrogen nuclear magnetic resonance (H¹-NMR) measurement of the compounds shown in Table 1 are shown in Table 2, and the values of the carbon 13 nuclear magnetic resonance (C¹³-NMR) measurement of these compounds are shown in Table 3. The corresponding carbon numbers of C¹³-NMR are shown in Table 4. Namely, carbon atoms in Table 3 are indicated by the carbon numbers shown in Table 4.

TABLE 2

| Synthesis Example No. | $H^1$—NMR: (CDCl$_3$) δ(ppm) |
|---|---|
| 1. | 5.14(s, NH), 2.80(s, NCH$_3$), 1.52(s, C(CH$_3$)$_2$) |
| 2. | 5.13(s, NH), 2.80(s, NCH$_3$), 1.95(q, C(CH$_3$)(C$\underline{H}_2$CH$_3$)), 1.45(s, C(C$\underline{H}_3$)(CH$_2$CH$_3$)), 0.66(t, C(CH$_3$)(CH$_2$C$\underline{H}_3$)) |
| 3. | 5.12(s, NH), 3.73(q, N(C$\underline{H}_2$CH$_3$)(C$_6$H$_5$CH$_3$)), 1.52(s, C(CH$_3$)$_2$) |
| 4. | 5.13(s, NH), 3.36(q, N(C$\underline{H}_2$CH$_3$)$_2$), 1.95(q, C(CH$_3$)(C$\underline{H}_2$CH$_3$)), 1.44(s, C(C$\underline{H}_3$)(CH$_2$CH$_3$)), 0.66(t, C(CH$_3$)(CH$_2$C$\underline{H}_3$)) |
| 5. | 5.19(s, NH), 2.78(s, NCH$_3$), 2.00(s, C(C$\underline{H}_3$)(C$_6$H$_5$)) |
| 6. | 5.16(s, NH), 2.78(s, NCH$_3$), 0.69(d, C(CH$_3$)(CH$_2$CH(C$\underline{H}_3$)$_2$)) |
| 7. | 5.12(s, NH), 2.80(s, NCH$_3$) |
| 8. | 5.14(s, NH), 3.36(q, N(C$\underline{H}_2$CH$_3$)$_2$), 1.53(s, C(CH$_3$)$_2$) |
| 9. | 5.14(s, NH), 3.30(q, N(C$\underline{H}_2$CH$_3$)(CH$_2$CH$_2$CH(CH$_3$)$_2$)), 1.53(s, C(CH$_3$)$_2$) |
| 10. | 5.12(s, NH), 3.30(q, N(C$\underline{H}_2$CH$_3$)(CH$_2$CH$_2$CH(CH$_3$)$_2$)), 1.96(t, C(CH$_3$)(C$\underline{H}_2$CH$_3$)), 1.45(s, C(C$\underline{H}_3$)(CH$_2$CH$_3$)), 0.66(t, C(CH$_3$)(CH$_2$C$\underline{H}_3$)) |
| 11. | 5.12(s, NH), 3.73(q, N(C$\underline{H}_2$CH$_3$)(C$_6$H$_5$CH$_3$)), 1.95(q, C(CH$_3$)(C$\underline{H}_2$CH$_3$)), 1.44(s, C(C$\underline{H}_3$)(CH$_2$CH$_3$)), 0.65(t, C(CH$_3$)(CH$_2$C$\underline{H}_3$)) |

TABLE 3

| Synthesis Example No. | $C^{13}$—NMR: (CDCl$_3$) δ(ppm) |
|---|---|
| 1. | 169.0(C-6), 142.1(C-4), 141.8(C-1), 127.2(C-2), 115.0(C-3), 41.7(C-7), 31.4(C-9), 31.4(C-8), 18.3(C-5) |
| 2. | 169.6(C-6), 141.9(C-4), 141.5(C-1), 128.1(C-2), 115.4(C-3), 45.2(C-7), 34.2(C-10), 31.1(C-8), 27.1(C-9), 18.0(C-5), 9.3(C-11) |
| 3. | 169.4(C-6), 143.6(C-10), 142.2(C-4), 142.0(C-1), 135.0(C-13), 130.5(C-12), 127.4(C-2), 127.0(C-11), 115.1(C-3), 46.8(C-8), 41.6(C-7), 31.0(C-15), 21.0(C-14), 18.1(C-5), 12.4(C-9) |
| 4. | 169.7(C-6), 142.1(C-4), 141.7(C-1), 128.3(C-2), 115.5(C-3), 45.0(C-7), 44.4(C-8), 34.2(C-11), 26.7(C-10), 17.6(C-5), 12.5(C-9), 9.3(C-12) |
| 5. | 169.5(C-6), 142.4(C-4), 140.7(C-1), 134.2(C-10), 129.3(C-2), 129.1(C-12), 128.6(C-11), 125(C-13), 115.0(C-3), 51.2(C-7), 31.1(C-8), 30.4(C-9), 18.0(C-5) |
| 6. | 169.5(C-6), 141.8(C-4), 141.8(C-1), 128.0(C-2), 115.3(C-3), 50.6(C-10), 45.3(C-7), 31.1(C-8), 28.2(C-9), 25.1(C-2), 24.6(C-11), 18.0(C-5) |
| 7. | 169.4(C-6), 142.0(C-4), 140.6(C-1), 127.8(C-2), 115.8(C-3), 45.1(C-7), 37.4(C-9), 31.1(C-8), 26.6(C-11), 23.0(C-10), 17.9(C-5) |
| 8. | 169.6(C-6), 142.3(C-4), 142.0(C-1), 127.4(C-2), 115.1(C-3), 44.4(C-8), 41.5(C-7), 31.0(C-10), 17.9(C-5), 12.5(C-9) |
| 9. | 169.5(C-6), 142.9(C-1), 142.6(C-4), 127.6(C-2), 115.2(C-3), 48.8(C-10), 45.0(C-8), 41.5(C-7), 36.1(C-11), 30.9(C-14), 26.4(C-12), 22.5(C-13), 18.2(C-5), 12.3(C-9) |
| 10. | 169.6(C-6), 141.9(C-4), 141.4(C-1), 128.0(C-2), 115.4(C-3), 48.7(C-10), 45.1(C-8), 45.0(C-7), 36.1(C-11), 34.2(C-15), 27.1(C-14), 26.3(C-12), 22.6(C-13), 18.0(C-5), 12.4(C-9), 9.3(C-16) |
| 11. | 169.7(C-6), 143.5(C-10), 141.8(C-4), 141.8(C-1), 135.2(C-13), 130.4(C-12), 128.0(C-2), 127.0(C-11), 115.5(C-3), 46.6(C-8), 45.1(C-7), 34.2(C-16), 27.1(C-15), 21.0(C-14), 18.0(C-5), 12.5(C-9), 9.3(C-17) |

Note
The carbon numbers shown in Table 3 are as indicated in Table 4.

TABLE 4

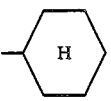

| Synthesis Example No. | R₁ | R₂ | R₃ | R₄ |
|---|---|---|---|---|
| 1 | —CH$_3$ | cyclohexyl | —CH$_3$ | —CH$_3$ |
| 2 | —CH$_3$ | cyclohexyl | —CH$_3$ | —CH$_2$CH$_3$ |
| 3 | —CH$_2$CH$_3$ | 4-methylphenyl | —CH$_3$ | —CH$_3$ |
| 4 | —CH$_2$CH$_3$ | —CH$_2$CH$_3$ | —CH$_3$ | —CH$_2$CH$_3$ |
| 5 | —CH$_3$ | cyclohexyl | —CH$_3$ | phenyl |
| 6 | —CH$_3$ | cyclohexyl | —CH$_3$ | —CH$_2$CH(CH$_3$)$_2$ |
| 7 | —CH$_3$ | cyclohexyl | —CH$_2$CH$_2$CH$_2$CH$_2$CH$_2$— (R₃ and R₄ joined) | |
| 8 | —CH$_2$CH$_3$ | —CH$_2$CH$_3$ | —CH$_3$ | —CH$_3$ |
| 9 | —CH$_2$CH$_3$ | —CH$_2$—CH$_2$—CH(CH$_3$)CH$_3$ | —CH$_3$ | —CH$_3$ |
| 10 | —CH$_2$CH$_3$ | —CH$_2$—CH$_2$—CH(CH$_3$)CH$_3$ | —CH$_3$ | —CH$_2$—CH$_3$ |
| 11 | —CH$_2$CH$_3$ | 4-methylphenyl | —CH$_3$ | —CH$_2$CH$_3$ |

Example 1

By using an attritor, the following components were pulverized to form dispersions.

(Dispersion A)

Condensation product      20 parts by weight

| | |
|---|---|
| obtained in Synthesis Example 1 | |
| 10% Aqueous solution of polyvinyl alcohol | 20 parts by weight |
| Water | 60 parts by weight |
| (Dispersion B) | |
| Bisphenol A | 15 parts by weight |
| Calcium carbonate | 5 parts by weight |
| 10% Aqueous solution of polyvinyl alcohol | 20 parts by weight |
| Water | 60 parts by weight |

The dispersions A and B were mixed with stirring at a weight ratio of 1/5 to form a heat-sensitive coloring layer-forming coating liquid. The coating liquid was coated on the surface of a commercially available wood-free paper by using a wire bar and dried to form a heat-sensitive color-forming layer having a basis weight of 5 g/m². The coated paper was calendered to form a heat-sensitive recording sheet.

Example 2

A heat-sensitive recording sheet was prepared in the same manner as described in Example 1 except that the condensation product synthesized in Synthesis Example 2 was used instead of the fluoran condensation product of the dispersion A.

Example 3

A heat-sensitive recording sheet was prepared in the same manner as described in Example 1 except that the condensation product synthesized in Synthesis Example 4 was used instead of the fluoran condensation product of the dispersion A.

Example 4

A heat-sensitive recording sheet was prepared in the same manner as described in Example 1 except that the condensation product synthesized in Synthesis Example 5 was used instead of the fluoran condensation product of the dispersion A.

Comparative Example 1

A heat-sensitive recording sheet was prepared in the same manner as described in Example 1 except that 3-(N-methyl-N-cyclohexylamino)-6-methyl-7-anilinofluoran widely used in the art was used instead of the fluoran condensation product of the dispersion A.

Each of the five recording materials obtained in the foregoing examples and comparative example was heated at 150° C. under a pressure of 1 kg/cm² for 0.5 second by a thermal gradient tester. The colored surface of the sample was covered with a food-packaging polyvinyl chloride wrap film containing a plasticizer and the sample was allowed to stand at 30° C. under a load of 250 g/cm² for 24 hours. Fading of the color of the colored image was checked with the naked eye. Furthermore, more, cotton seed oil was coated on the colored surface of the sample and the sample was allowed to stand at 39° C. for 24 hours. Fading of the color was checked with the naked eye.

The obtained results are shown in Table 5.

TABLE 5

| | | Color Fading | |
|---|---|---|---|
| | Color Shade | Resistance to Plasticizer | Resistance to Cotton Seed Oil |
| Example 1 | blackish green | O | O |
| Example 2 | " | O | O |
| Example 3 | " | O | O |
| Example 4 | " | O | O |
| Comparative Example 1 | " | X | X |

Note
The resistance to the plasticizer and the resistance to cotton seed oil were evaluated as follows.
O: no practical significant color fading
X: color of the colored portion substantially came off and color fading was practically significant

Example 5

By using a paint conditioner, the following components were pulverized for 24 hours to form dispersions C, D and E.

| | |
|---|---|
| (Dispersion C) | |
| Condensation product obtained in Synthesis Example 1 | 25 parts by weight |
| 15% Aqueous solution of polyvinyl alcohol | 30 parts by weight |
| Water | 45 parts by weight |
| (Dispersion D) | |
| 3,4-Dihydroxyphenyl p-tolylsulfone | 25 parts by weight |
| 15% Aqueous solution of polyvinyl alcohol | 30 parts by weight |
| Water | 45 parts by weight |
| (Dispersion E) | |
| Diphenyl carbonate | 25 parts by weight |
| 15% Aqueous solution of polyvinyl alcohol | 30 parts by weight |
| Water | 45 parts by weight |

10 parts by weight of dispersion C, 25 parts by weight of dispersion D, 30 parts by weight of dispersion E, 30 parts by weight of 50% aqueous calcium carbonate dispersion and 5 parts by weight of 15% aqueous polyvinyl alcohol solution were mixed with stirring to form a coating liquid. The obtained coating liquid was coated on the surface of a substrate paper of 50 g/m² by using a wire bar to a dry coated weight of 10 g/m², thereby forming a heat-sensitive recording sheet.

Example 6

Dispersion F having the following composition was prepared as described in Example 5.

| | |
|---|---|
| (Dispersion F) | |
| Lauryl gallate | 25 parts by weight |
| 15% Aqueous solution of polyvinyl alcohol | 30 parts by weight |
| Water | 45 parts by weight |

Using 25 parts by weight of dispersion F with 10 parts by weight of dispersion C and 30 parts by weight of dispersion E as prepared in Example 5, a heat-sensitive recording sheet was prepared as described in Example 5.

Comparative Example 2

Dispersion G having the following composition was prepared as described in Example 5.

| (Dispersion G) | |
|---|---|
| 3-(N—methyl-N—cyclohexylamino)-6-methyl-7-anilinofluoran | 25 parts by weight |
| 15% Aqueous solution of polyvinyl alcohol | 30 parts by weight |
| Water | 45 parts by weight |

Using 10 parts by weight of dispersion G with 25 parts by weight of dispersion F as prepared in Example 6 and 30 parts by weight of dispersion E as prepared in Example 5, a heat-sensitive recording sheet was prepared as described in Example 5.

Comparative Example 3

A heat-sensitive recording sheet was prepared in the same manner as described in Example 1 except that bisphenol A was used instead of 3,4-dihydroxyphenyl p-tolylsulfone of the dispersion D.

Each of the five heat-sensitive recording sheets thus obtained was subjected to color developing treatment using a label printer (supplied by Ishida Kohki Co.). The colored surface of the sample was coated with a salad oil, plasticizer (dioctyl phthalate) and fluorescent color pen, the sample was allowed to stand at room temperature for 24 hours, and the fading of the color and the color developing on the non-color-developed area were checked with the naked eye. Further, the sample was allowed to stand at 60° C. for 24 hours and the color developing on the non-color-developed area was checked to evaluate the shelf stability.

TABLE 6

| Example No. | Resistance to Oil | Resistance to Plasticizer | Resistance to Fluorescent Pen | Shelf Stability |
|---|---|---|---|---|
| 5 | O | O | O | O |
| 6 | O | O | O | Δ |
| Comparative 2 | Δ | Δ | Δ | Δ |
| Comparative 3 | Δ | Δ | Δ | Δ |

Note
O: very good because of no fading on the colored and no color developing on the non-colored area
Δ: slight fading on the colored area or slight color developing on the non-colored area, but no practical problem
X: no practical use because of substantial discoloration on the colored area and significant color developing on the non-colored area

We claim:

1. A fluoran derivative of the following general formula:

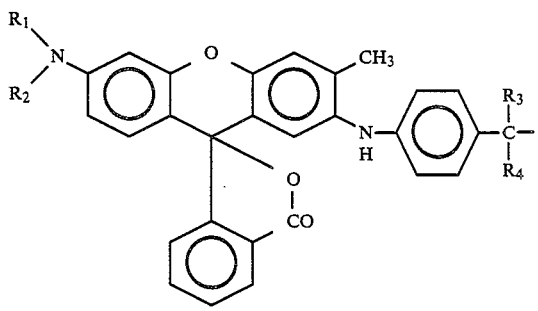

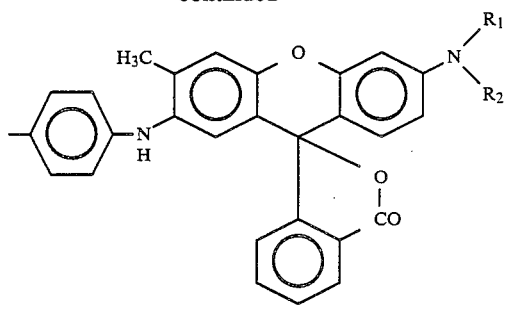

wherein $R_1$ and $R_2$, which may be the same or different, stand for an alkyl group having 1 to 9 carbon atoms, a cycloalkyl group having 3 to 6 carbon atoms, a phenyl group or a phenyl group substituted by an alkyl group having 1 to 4 carbon atoms, and $R_3$ and $R_4$, which may be the same or different, stand for an alkyl group having 1 to 6 carbon atoms, or a phenyl group or $R_3$ and $R_4$ may form a 5- to 8-membered cycloalkane together with the carbon atom to which they are bonded.

2. A fluoran derivative as set forth in claim 1, wherein $R_3$ and $R_4$ form, together with the carbon atom to which they are bonded, a ring selected from the group consisting of a cyclopentanone, cyclohexanone, cycloheptanone and cyclooctanone ring.

3. A fluoran derivative as set forth in claim 1, wherein the

group is selected from the following groups:

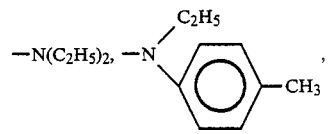

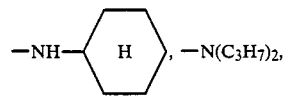

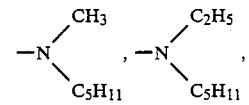

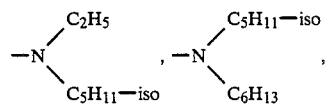

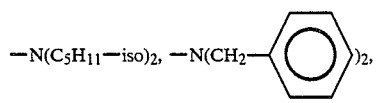

-continued
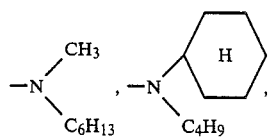
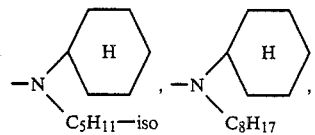
-continued
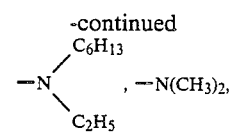
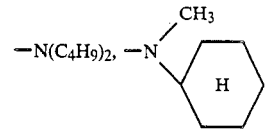
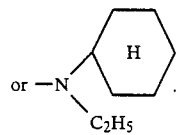
* * * * *